United States Patent [19]
Rock et al.

[11] Patent Number: 6,149,594
[45] Date of Patent: Nov. 21, 2000

[54] AUTOMATIC ULTRASOUND MEASUREMENT SYSTEM AND METHOD

[75] Inventors: Joseph E Rock, Littleton, Mass.; Carolyn Alexander, Atkinson, N.H.

[73] Assignee: Agilent Technologies, Inc., Palo Alto, Calif.

[21] Appl. No.: 09/305,612

[22] Filed: May 5, 1999

[51] Int. Cl.⁷ ...................................................... A61B 8/00
[52] U.S. Cl. ............................................................ 600/437
[58] Field of Search .................................... 600/437, 441, 600/442, 443, 447, 449, 458; 73/602; 128/921–924

[56] References Cited

U.S. PATENT DOCUMENTS

| | | | |
|---|---|---|---|
| 4,913,157 | 4/1990 | Pratt, Jr. et al. | 600/449 |
| 4,941,474 | 7/1990 | Pratt, Jr. | 600/442 X |
| 5,417,215 | 5/1995 | Evans et al. | 600/442 |
| 5,776,063 | 7/1998 | Dittrich et al. | 600/458 X |
| 5,878,746 | 3/1999 | Lemelson et al. | 128/922 X |

*Primary Examiner*—Francis J. Jaworski

[57] ABSTRACT

An automatic ultrasound measurement system reduces the necessary amount of user interaction by correlating the results of one or more basic ultrasound measurements with a known set of parameters corresponding to the diagnoses of various potential conditions to automatically provide the user with the most probable potential diagnoses and with recommendations for additional measurements relevant to those potential diagnoses.

24 Claims, 11 Drawing Sheets

32

Basic Set of Measurement and/or Calculation for Adult Cardiac Study

Adult Cardiac
    2D / M-mode
        Measurements
            Right Ventricular Dimension
            Interventricular Septum - diastole
            Left Ventricular Dimension - diastole
            Left Ventricular Posterior Wall - diastole
            Interventricular Septum - systole
            Left Ventricular Dimension - systole
            Left Ventricular Posterior Wall - systole
            Aortic Root Diameter
            Left Atrial Dimension Calculations
            Fractional Shortening
            Ejection Fraction Doppler
        Measurements
            Aortic peak systolic velocity
            Pulmonic peak systolic velocity
            Mitral peak systolic velocity
            Mitral deceleration time
            Tricuspid peak diastolic velocity
            Estimated Right Ventricular Systolic Pressure Calculations
            Aortic peak systolic gradient
            Pulmonic peak systolic gradient
            Mitral valve pressure half-time
            Mitral valve area

FIG. 3

AUTOMATIC ULTRASOUND MEASUREMENT SYSTEM AND METHOD

TECHNICAL FIELD

The present invention is generally related to ultrasound imaging systems, and more particularly, to a system and method for using the correlation between a set of basic ultrasound measurements and a known set of parameters corresponding to the diagnoses of various potential conditions to automatically provide the user with information useful in evaluating the patient's condition,

BACKGROUND OF THE INVENTION

Modern high performance ultrasound imaging systems are currently used for medical applications and other uses. Generally, such systems employ a sonic transducer to emit a sonic pulse through a medium, such as the human body, which generates sonic echoes. These echoes are received by the transducer or other sensors and captured in data that is stored and ultimately used to generate images on a display. Measurements are then taken from the display. In some systems the measurements are taken with such hand-held tools as rulers and calipers. Other systems incorporate electronic measurement tools into the display.

The information measurable from the display depends on the operational mode of the ultrasound image. Current ultrasound systems allow the use of several operational modes, including a two-dimensional (2-D) mode (also sometimes referred to as "B-mode"), a Doppler mode, and a motion mode (M-mode). Each of these operational modes allows the ultrasound system user to obtain different ultrasound measurements: the 2-D mode allows the user to measure distances, areas and volumes directly from the display. The Doppler mode allows the user to obtain measurements from the display that indicate velocities. The M-mode allows the user to measure the movement of structures in one-dimension over time.

In making a diagnosis from ultrasound images, physicians typically rely on adequate image quality, acquisition of proper views, and sufficient quantification of all relevant structures and flows. Although image quality is usually constant within a system and acquisition of proper views is typically associated with a standard protocol within each lab, quantification of all relevant information is particularly problematic. In present ultrasound systems, the user must have sufficient knowledge of the structures and flows associated with various diagnoses to interpret the results of the ultrasound measurements. Typically, the need for additional measurements and the type of additional measurements needed are determined by each user based on his or her knowledge and interpretation of the ultrasound views.

Some efforts have been made to automate ultrasound measurement systems. However, these efforts have still involved significant user interaction to interpret the views, to make decisions regarding the need for additional ultrasound measurements, and to make appropriate diagnoses.

Thus, a heretofore unaddressed need exists in the industry for an automatic ultrasound measurement system and method that reduces the necessary amount of user interaction by automatically analyzing ultrasound measurements to provide the user with a list of the most likely diagnoses and to recommend additional ultrasound measurements relevant to confirming the diagnosis.

SUMMARY OF THE INVENTION

The present invention provides a system and method for automatically analyzing ultrasound measurements by correlating the results of a baseline set of ultrasound measurements that are commonly performed in most ultrasound studies to a known set of parameters corresponding to the diagnoses of various potential conditions to automatically provide the user with information useful in evaluating the patient's condition.

Briefly described, the system can be implemented as follows: the system is provided with means for accessing a template set of ultrasound measurements and calculations that correspond to the possible diagnoses for which an ultrasound study is being performed. The template set may be defined by the user. In one embodiment of the invention, the template set is provided on a CD-ROM and stored in the system memory. Each template in the template set defines the threshold value of at least one basic ultrasound measurement indicative of the diagnosis corresponding to that template. The system also has means for obtaining ultrasound data corresponding to an ultrasound measurement performed on a patient, as well as means for automatically correlating the ultrasound data with the template set of possible diagnoses to determine whether any of the possible diagnoses in the template set are indicated by the ultrasound data.

The present invention can also be viewed as providing a method for operating an ultrasound measurement system as follows: first, a template set (TS) of possible diagnoses is defined. The TS is comprised of templates which define the ultrasound measurements and calculations that correspond to the diagnoses of potential medical conditions. Each of the templates in the TS must define the threshold value of at least one basic ultrasound measurement indicative of the diagnosis corresponding to that template. Once the template set has been defined, one or more ultrasound measurements from a basic set of the most commonly performed measurements is performed on the patient to obtain ultrasound data. The ultrasound data is then automatically correlated with the TS. The results of this correlation are used by the invention to determine automatically whether any of the potential diagnoses in the TS are indicated by the ultrasound data. These results may also be used by the invention to determine automatically additional measurements that may be relevant to confirming the diagnoses. The invention then automatically displays a list of potential diagnoses and additional recommended measurements to the user.

Other features of the present invention will become apparent to one with skill in the art upon examination of the following drawings and detailed description. It is intended that all such additional features be included herein within the scope of the present invention.

BRIEF DESCRIPTION OF THE SEVERAL VIEWS OF THE DRAWINGS

The invention can be better understood with reference to the following drawings. The components in the drawings are not necessarily to scale, emphasis instead being placed upon clearly illustrating the principles of the present invention. Moreover, in the drawings, like reference numerals designate corresponding parts throughout the several views.

FIG. 3 is a specific listing of the basic set of ultrasound measurements of FIG. 2 which may be selected for an adult cardiac ultrasound study;

Figure 1:
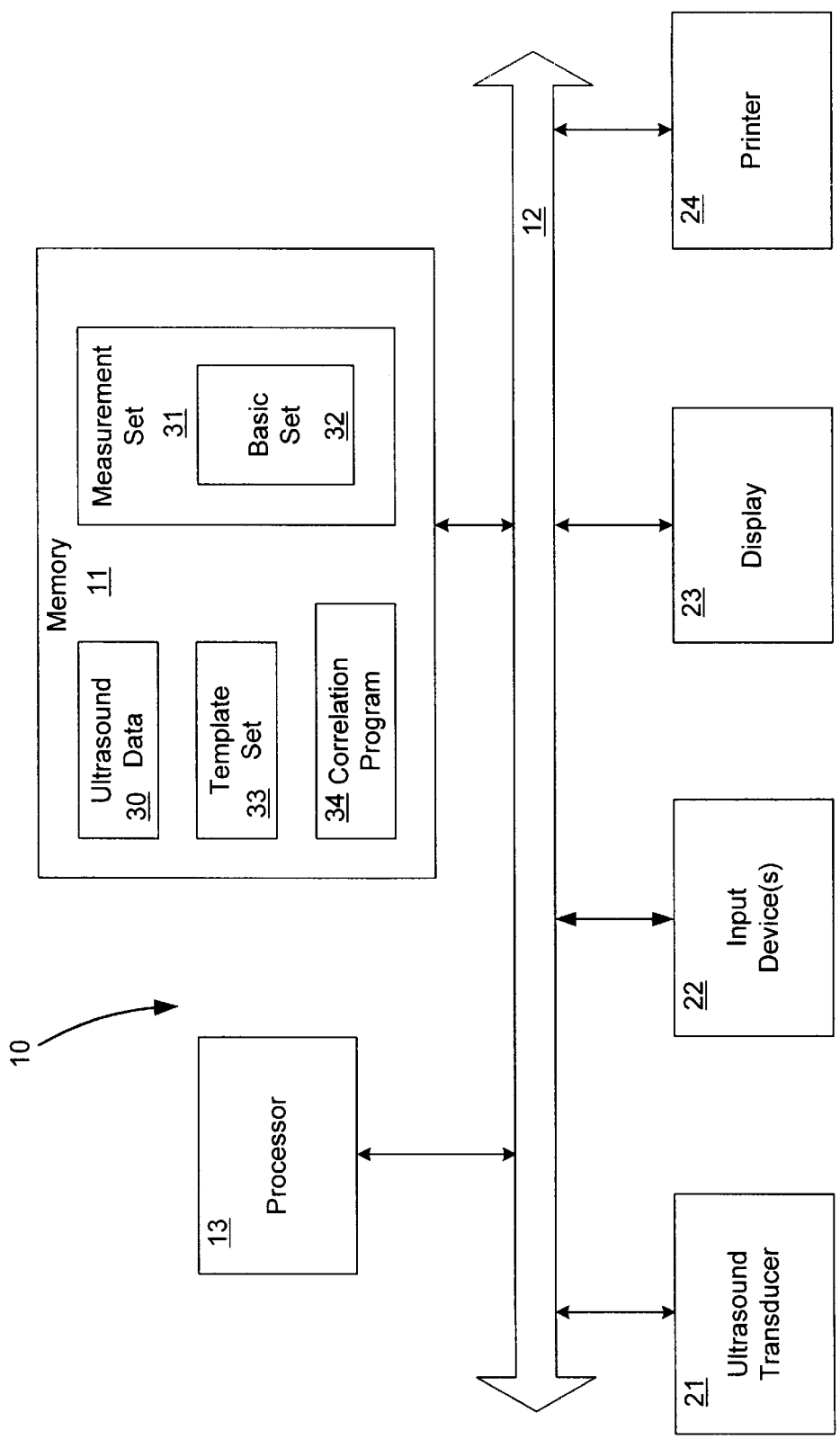
FIG. 1 is a simplified schematic view of an ultrasound measurement system.

Reference will now be made in detail to the description of the invention as illustrated in the drawings. While the invention will be described in connection with these drawings, there is no intent to limit it to the embodiment or embodiments disclosed therein. On the contrary, the intent is to cover all alternatives, modifications and equivalents included within the spirit and scope of the invention as defined by the appended claims.

DETAILED DESCRIPTION OF THE PREFERRED EMBODIMENT

FIG. 1 is a simplified schematic view of an ultrasound measurement system 10. In this system 10, memory 11 and processor 13 interface with user devices such as ultrasound transducer 21, input devices 22 (which may be such devices as electronic calipers and tracers), display 23 and printer 24, through interface 12. Ultrasound data 30 pertinent to the patient under study, which is comprised of the results of various ultrasound measurements and calculations, is measured, processed, and stored in memory 11. The memory 11 also contains at least the following: (1) a measurement set ("MS") 31 of the ultrasound measurements and calculations that the system is capable of performing; (2) a basic measurement set ("BMS") 32, which is a subset of the MS; and (3) a template set ("TS") 33, which consists of templates defining diagnoses for various potential conditions according to the measurements and calculations in the MS. Also resident in memory 11 is correlation program 34.

The correlation program 34, which comprises an ordered listing of executable instructions for implementing logical functions, can be embodied in any computer-readable medium for use by or in connection with an instruction execution system, apparatus, or device, such as a computer-based system, processor-containing system, or other system that can fetch the instructions from the instruction execution system, apparatus, or device and execute the instructions. In the context of this document, a "computer-readable medium" can be any means that can contain, store, communicate, propagate, or transport the program for use by or in connection with the instruction execution system, apparatus, or device. The computer readable medium can be, for example but not limited to, an electronic, magnetic, optical, electromagnetic, infrared, or semiconductor system, apparatus, device, or propagation medium. More specific examples (a nonexhaustive list) of the computer-readable medium would include the following: an electrical connection (electronic) having one or more wires, a portable computer diskette (magnetic), a random access memory (RAM) (magnetic), a read-only memory (ROM) (magnetic), an erasable programmable read-only memory (EPROM or Flash memory) (magnetic), an optical fiber (optical), and a portable compact disc read-only memory (CDROM) (optical). Note that the computer-readable medium could even be paper or another suitable medium upon which the program is printed, as the program can be electronically captured, via for instance optical scanning of the paper or other medium, then compiled, interpreted or otherwise processed in a suitable manner if necessary, and then stored in a computer memory.

With reference to FIG. 1, the following is a brief overview of the system 10 of the invention: an initial ultrasound test is performed on the patient, as requested by a physician. The initial ultrasound test consists of at least one of the measurements and calculations from the MS 31, at least one of which must also be part of the BMS 32. It is not necessary for the user to have any knowledge with respect to the patient's health or potential diagnoses. The only required parameters are that the initial test include at least one measurement or calculation from the BMS, and that each of the potential diagnoses in the TS also include at least one measurement or calculation from the BMS. These requirements are typically satisfied by defining the BMS to include the most widely used initial screening measurements and calculations for the conditions included in the TS.

Once the initial test is performed, the results of the initial test are stored as ultrasound data 30 in memory 11. The correlation program 34 then automatically correlates the ultrasound data 30 with the TS 33, and provides the user with a listing of potential diagnoses, typically on the display 23. The correlation program 34 may be configured to automatically rank these diagnoses according to their relative probabilities. The correlation program 34 also may be configured to automatically use the correlation of the ultrasound data 30 with the TS 33 to recommend additional measurements from the MS 31. In this way, the system may be configured to automatically provide the user with a ranked list of the most likely diagnoses, as well as a ranked list of additional recommended measurements from the MS 31. The system function is described in greater detail hereinbelow.

Figure 2:
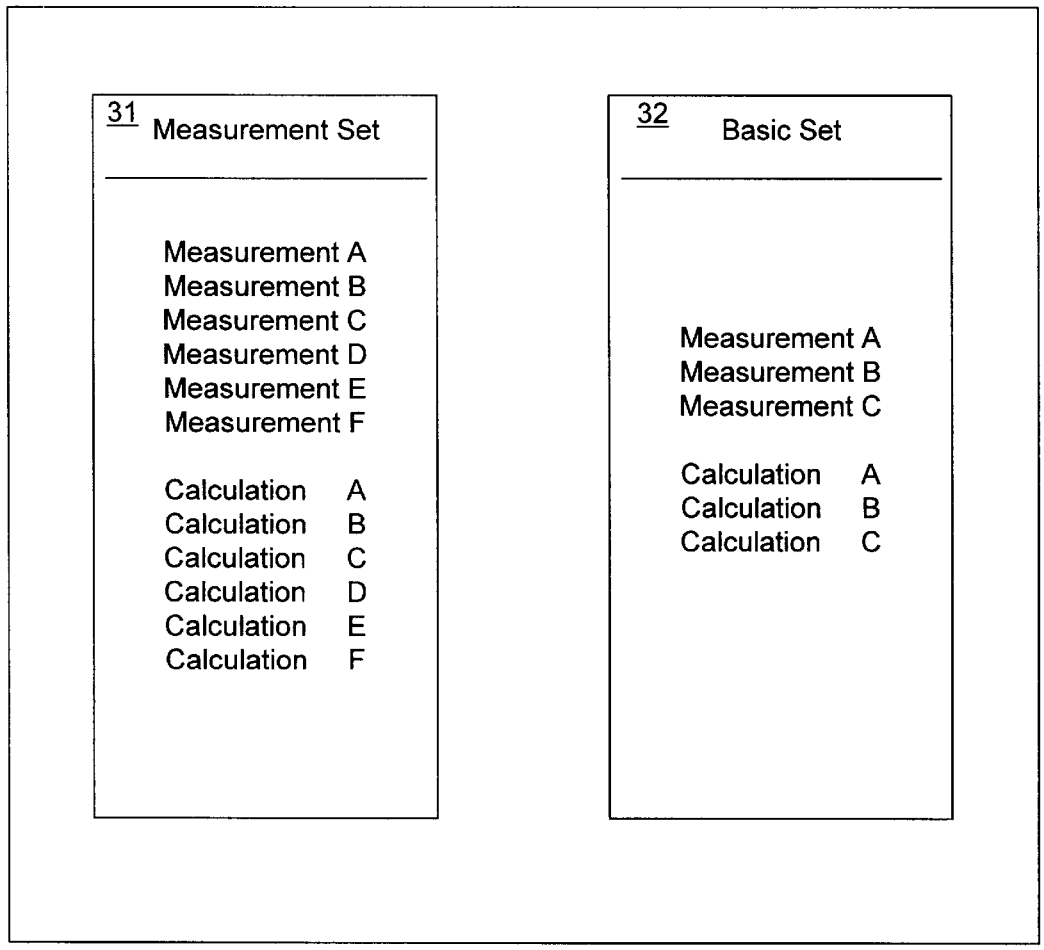
FIG. 2 is a block diagram of a basic set of ultrasound measurements, which is typically stored in the memory of FIG. 1.

FIG. 2 illustrates, in the form of block diagrams, the MS 31 and BMS 32 of FIG. 1. FIG. 2 illustrates that the BMS 32 is a subset of MS 31. In the example illustrated in FIG. 2, the MS 31 is comprised of Measurements A, B, C, D, E and F and Calculations A, B, C, D, E and F, while the BMS 32 is comprised of Measurements A, B and C and Calculations A, B and C.

FIG. 3 is an example of an actual listing of the ultrasound measurements and calculations that may be included in the BMS 32 for an adult cardiac study. The BMS for other ultrasound studies, such as fetal development studies, may include other measurements and calculations from the MS. The calculations illustrated in FIGS. 2 and 3 are relationships between measurements, which are typically calculated by the ultrasound system. For example, Calculation D of FIG. 2 may be defined as the relationship between Measurement A and Measurement B.

Figure 4:
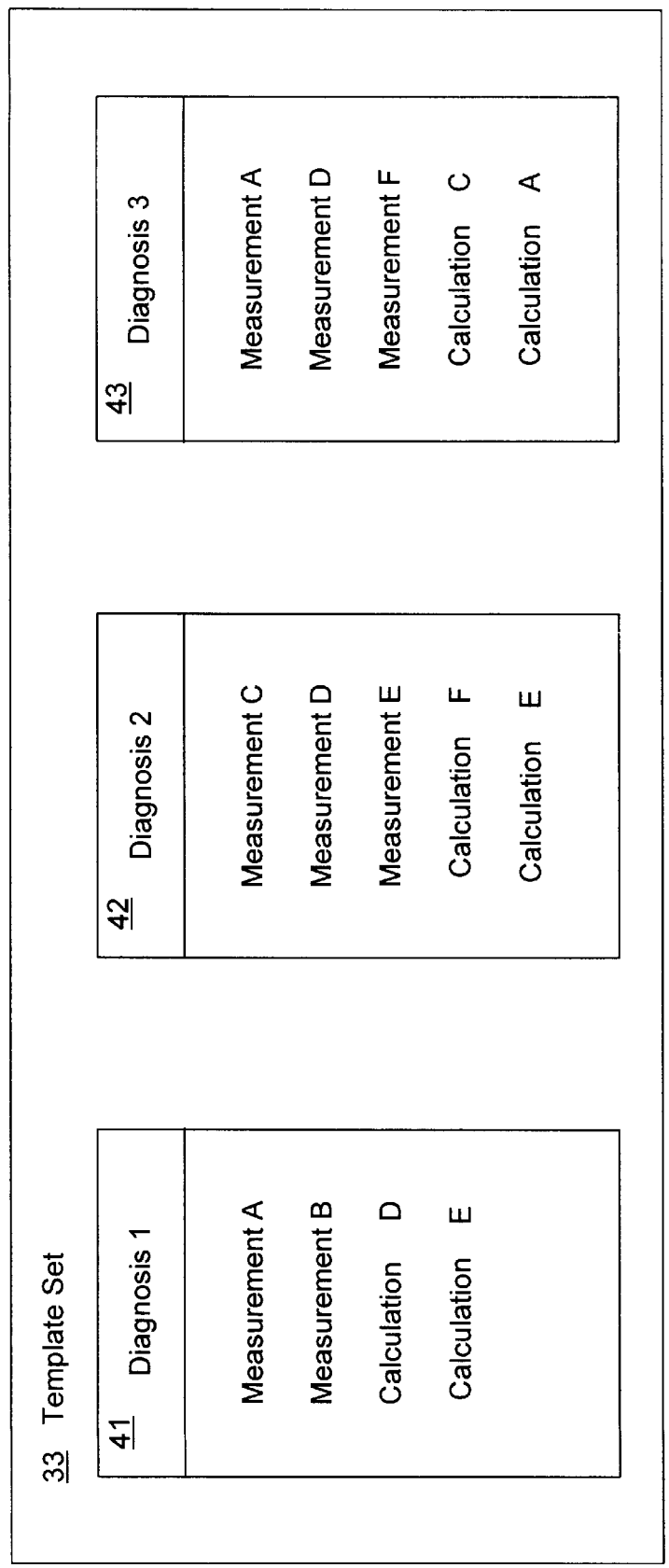
FIG. 4 is a block diagram of a template set of potential diagnoses corresponding to various conditions, which is typically stored in the memory of FIG. 1.

FIG. 4 is a block diagram of a TS 33 of diagnoses corresponding to various conditions, which is typically stored in memory 11 of FIG. 1. This diagram defines separate templates 41, 42 and 43 for each potential diagnosis (i.e., Diagnosis 1, Diagnosis 2, Diagnosis 3) in the TS 33, in terms of the measurements in the MS, and calculations related to those measurements, that are pertinent to that particular diagnosis. The measurements and calculations listed in each template are ranked in the order of their importance to that particular diagnosis. For example, with reference to FIG. 4, Measurement A is the most important measurement for Diagnosis 1 and Diagnosis 3, while Measurement C is the most important measurement for Diagnosis 2.

Using the MS and BMS illustrated in FIG. 2, and the TS illustrated in FIG. 4 as examples, the system of FIG. 1 illustratively could operate by initially obtaining ultrasound data 30 by performing Measurement C. The correlation program 34 will then correlate the ultrasound data 30 with the TS 33. In this example, it is assumed that this correlation reveals that Measurement C is outside of normal parameters for template 42 (Diagnosis 2), in which case the system will list Diagnosis 2 as the most likely potential diagnosis, and recommend additional measurements and calculations associated with Diagnosis 2 to aid the user in further diagnosing the patient's condition.

Figure 5:
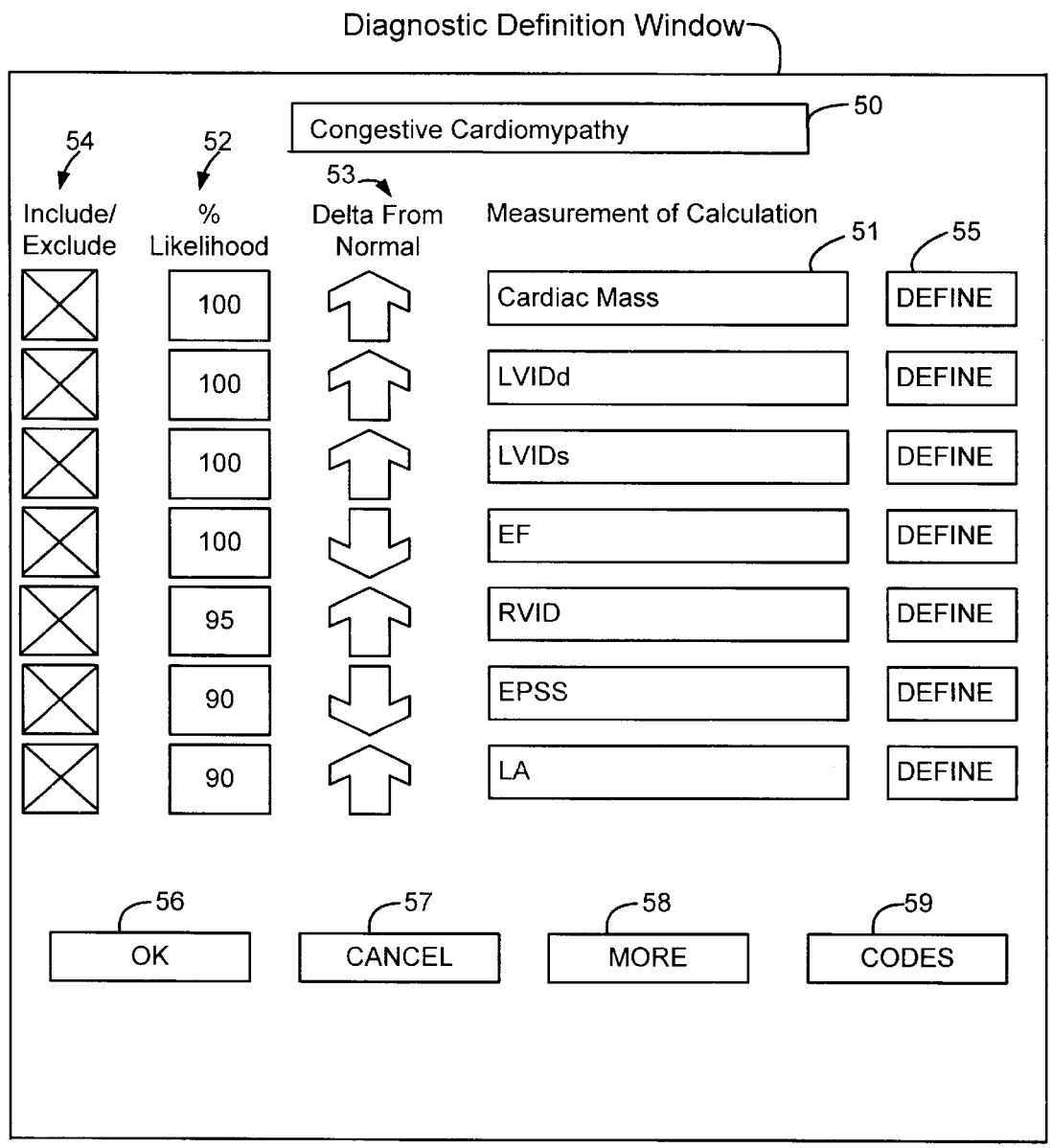
FIG. 5 is a schematic diagram of an interface for use in defining the template for one of the diagnoses depicted in FIG. 2.

FIGS. 5, 6, 7 and 8 illustrate one method for defining the templates in the TS. FIG. 5 is a schematic diagram of an input device, depicted in FIG. 5 as a computer input screen, which is referred to hereinafter as the "diagnosis definition window". The diagnosis definition window may be used to define the measurements and calculations that make up the template for each potential diagnosis. Only the measurements and calculations pertinent to the particular potential diagnosis are included within the template for that diagnosis.

The following discussion assumes that the template for each condition is defined by the user as part of the initial system set up. However, in one embodiment of the invention the pertinent templates are pre-defined and are resident in the ultrasound system memory. In an alternative embodiment, the templates may be pre-defined by reference to applicable medical literature and supplied to the user in an appropriate form, such as a CD-ROM, which is read by the system and stored in the system memory. In any case, the following discussion illustrates criteria that may be used to define the templates for various conditions.

With reference to FIG. 5, the particular condition for which a template is being defined is first given a unique name 50, which is illustratively "congestive cardiomyopathy." Next, the particular measurements and calculations relevant to that condition are supplied in field 51. Pertinent information regarding each measurement and calculation is provided in fields 52 and 53. The percentage of the time that the associated measurement or calculation is indicated in the diagnosis is entered in field 52. Field 53 indicates whether the associated measurement or calculation indicative of the diagnosis is higher or lower than the normal values for that measurement or calculation. Thus, in the example illustrated in FIG. 5, the measurement "LA" is indicated in the diagnosis of congestive cardiomyopathy 90% of the time (field 52), and a higher than normal value for measurement "LA" is indicative of that diagnosis (field 53).

As discussed hereinbelow, the pertinent information regarding each measurement and calculation is used by the correlation program 34 of FIG. 1 in determining the likelihood that the patient has the defined condition.

In most cases, each of the pertinent measurements and calculations that make up the template is included in the decision process in determining whether the patient has the defined condition. However, as illustrated in FIG. 5, the user has the option of using field 54 to exclude a particular measurement or calculation from the decision process in a particular case. In the example of FIG. 5, the measurement EF is excluded from the decision process. This option is made available to the user so that patients known to have abnormal readings for certain measurements for other reasons will not register a false positive for the defined diagnosis.

Figure 6:
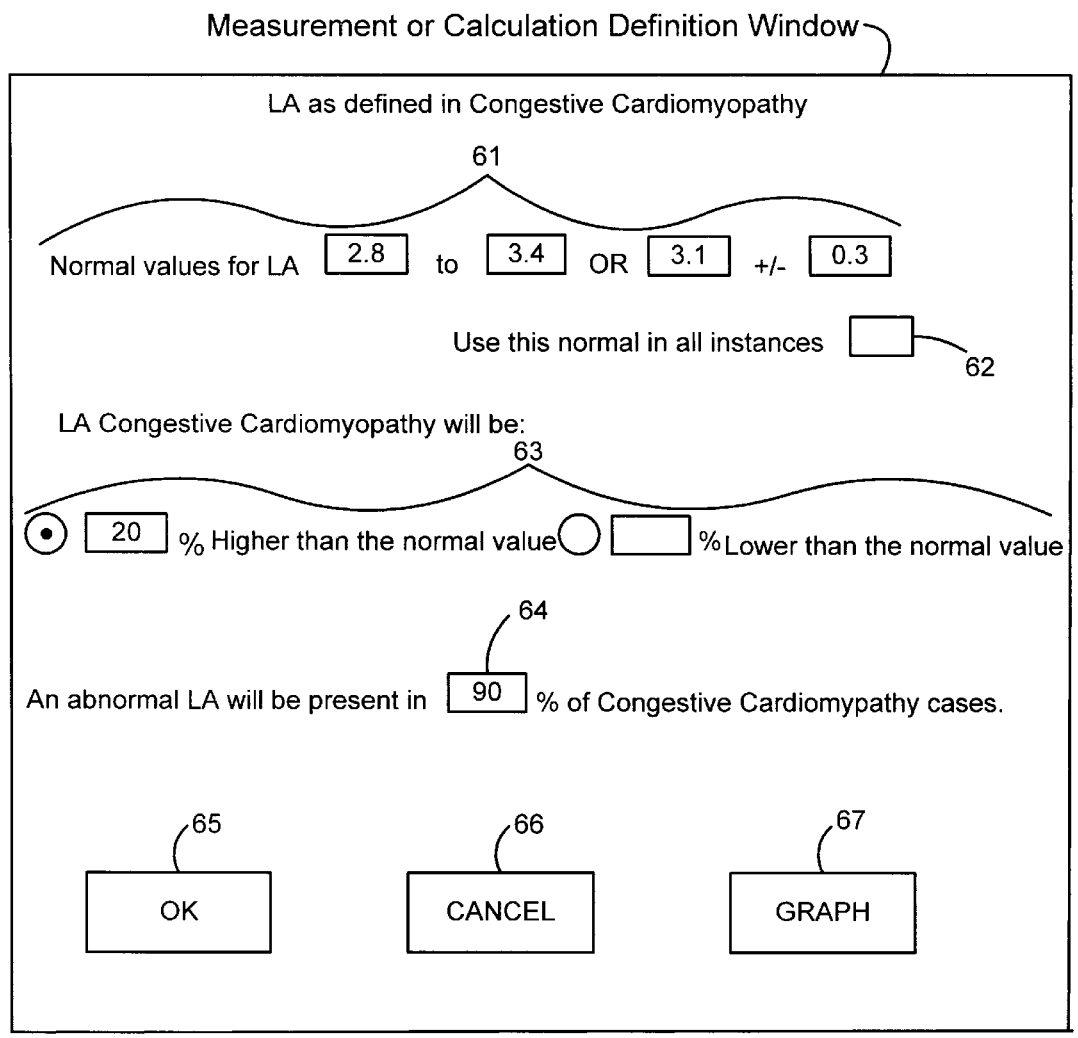
FIG. 6 is a schematic diagram of an interface for use in defining the elements of one of the measurements of the template of FIG. 5.
Figure 8:
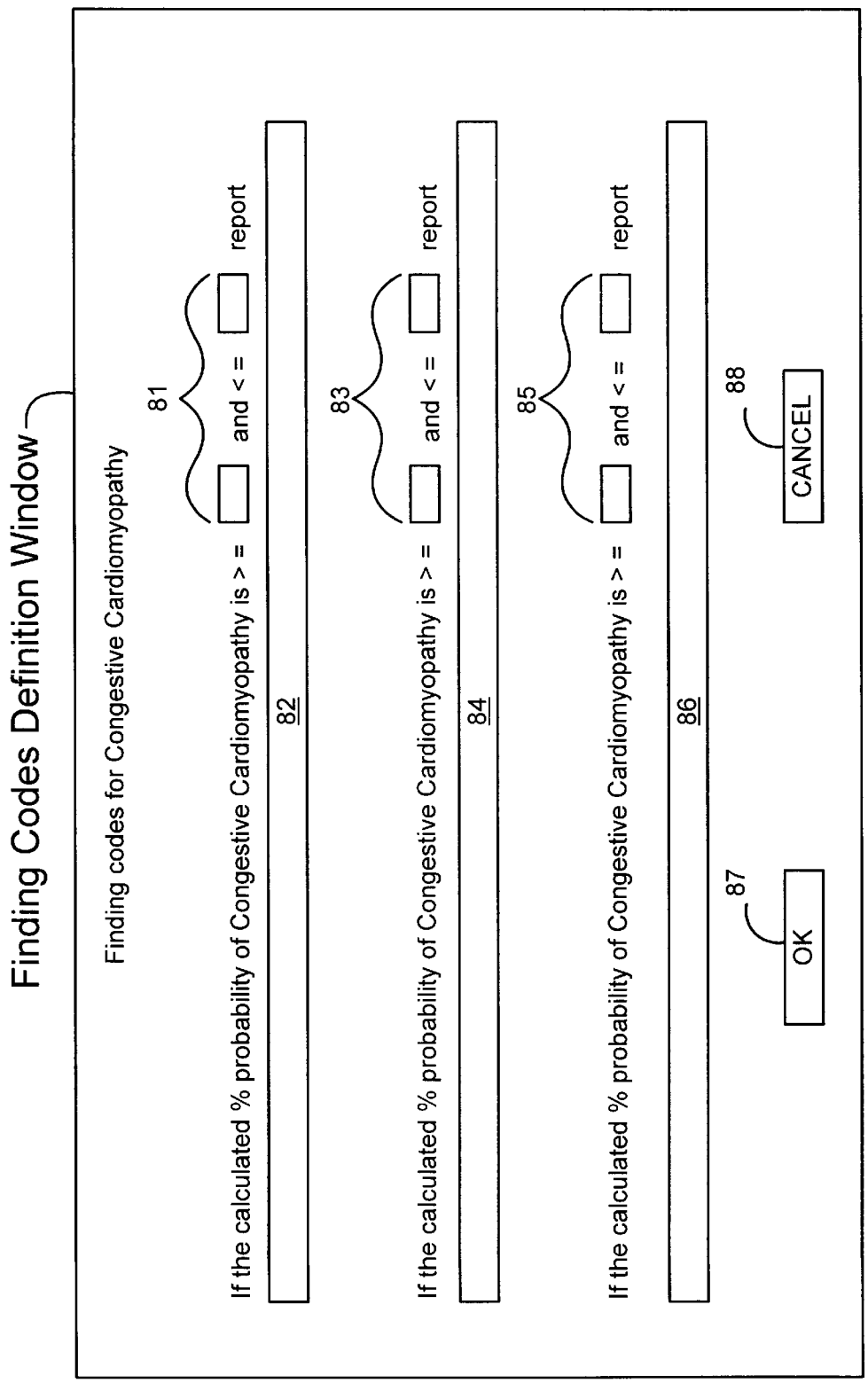
FIG. 8 is a schematic diagram of an interface for use in defining additional information to be included in the template of FIG. 5.

In this example, each measurement and calculation has its own associated DEFINE command button in field 55, which takes the user to another screen, such as depicted in FIG. 6, for defining the specific measurement or calculation. Other command buttons illustrated in FIG. 5 are OK 56, which closes the window and saves the definition, CANCEL 57, which closes the window and aborts the definition, MORE 58, which provides access to additional lines for including more measurements and calculations in the definition, and CODES 59, which takes the user to another screen, such as depicted in FIG. 8, for defining additional information associated with the defined diagnosis.

FIG. 6 illustrates one method of defining the measurement and calculations of FIG. 5. With reference to FIG. 6, which illustrates a computer screen referred to hereinafter as the "measurement or calculation definition window", the user provides some basic information about each specific measurement and calculation, and how each measurement and calculation pertains to the diagnosis for the condition for which the template is being defined.

In the example illustrated in FIG. 6, the user is defining the parameters of the measurement "LA" of FIG. 5. First, the user defines the normal value for this measurement in field 61. In the embodiment illustrated in FIG. 6, the normal value is entered either as a range (i.e., 2.8 to 3.4), or as a mean value with a variance (i.e., 3.1±0.3).

In this example, the user is also asked in field 62 whether this normal value defined in the measurement definition window should be used for all instances of the measurement "LA", or if the defined normal value is unique to the condition of congestive cardiomyopathy. If the user indicates in field 62 that the defined normal is to be used in all instances, there will be no need to re-define the measurement "LA" in creating the templates for other conditions for which this measurement is pertinent. On the other hand, the example illustrates the flexibility that can be used in defining a measurement. If the measurement "LA" is more or less critical to the diagnosis of another potential condition, the defined normal may be re-defined in the template for that condition.

FIG. 6 also illustrates additional information which may be included within the measurement definition. For example, the user may indicate in field 63 whether the measurement will be higher or lower than normal if the subject condition is present. In the example illustrated in FIG. 6, an LA measurement of 20% higher than normal is defined to indicate the presence of congestive cardiomyopathy.

The user will also provide information in field 64 about how often this measurement or calculation can be found to be abnormal in the anomaly being described. In the example of FIG. 6, an abnormal LA measurement is present in 90% of congestive cardiomyopathy cases. As discussed hereinbelow with respect to FIGS. 9A, 9B and 9C, this percentage can be used by the correlation program to automatically determine the likelihood that the patient has congestive cardiomyopathy and to rank this potential diagnosis with other potential diagnoses that may be indicated for that particular patient.

Figure 7:
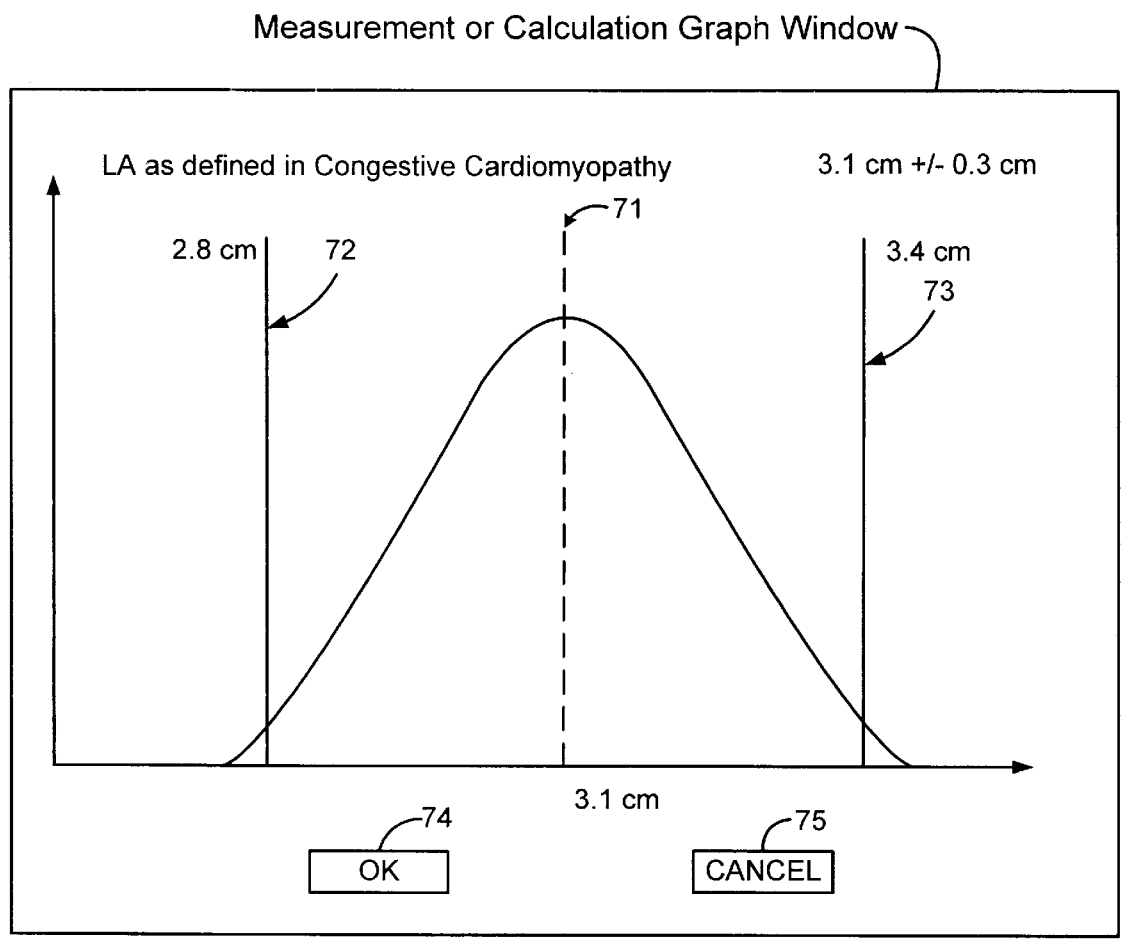
FIG. 7 is a schematic diagram of an alternative interface for use in defining an element of one of the measurements of the template of FIG. 5.

The command buttons illustrated in FIG. 6 are OK 65, which allows the user to exit the window and save the definition, CANCEL 66, which allows the user to exit the window and abort the definition, and GRAPH 67, which takes the user to another screen, such as depicted in FIG. 7, for an alternative method of defining the normal values for the measurement.

With reference to FIG. 7, which illustrates a computer screen referred to hereinafter as the "measurement or calculation graph window", the illustrated distribution of the LA measurement may be taken from relevant medical literature or other conventional sources. Alternatively, if the user has selected to use a previously defined normal in all instances and then proceeds to the graph page illustrated in FIG. 7, the graph will default to the user defined normal rather than the published normal.

With reference to FIG. 7, the dashed line 71 indicates the mean value of the measurement. The two solid vertical lines 72 and 73 indicate the position of ±2 standard deviations from the mean reported in the literature. Using some means of control, such as a mouse, the user moves these vertical lines along the horizontal axis to select the normal range for the measurement. As the user moves the vertical bars, the mean and normal values update automatically.

The user may exit the window illustrated in FIG. 7 either by selecting the OK command button 74, which will close the window and save the definition, or by selecting the CANCEL command button 75, which will close the window and abort the definition.

FIG. 8 illustrates a computer screen referred to hereinafter as the "finding codes definition window", which is accessed by the CODES command button 59 of FIG. 5. This screen allows the user to include within the template information to be displayed based on the findings made by the correlation program when the ultrasound data for a particular patient is correlated with that template.

With reference to FIG. 8, the term "finding code" is used to refer to information associated with the findings or results of the correlation program for a particular template. In the illustrative example of FIG. 8, the user is able to define three different finding codes for the diagnosis of congestive cardiomyopathy, depending on the results obtained by the correlation program. For example, the user may indicate in field 81 that "if the calculated % probability of congestive cardiomyopathy is >=75 and <=100" the illustrative text string "presence of congestive cardiomyopathy is noted", which is entered in field 82, should be displayed. Similarly, the user may define a lower range of probabilities in field 83, such as >=50 and <=74, to correspond to the illustrative text string "further testing for congestive cardiomyopathy indicated", which is entered in field 84. The user may define a still lower range of probabilities in field 85, such as >=0 and <=5, to correspond to the illustrative text string "presence of congestive cardiomyopathy highly unlikely", which is entered in field 86. The bounds for different finding codes should not be allowed to overlap, as this could result in ambiguous findings.

The user may exit the window illustrated in FIG. 8 either by selecting the OK command button 87, which will close the window and save the definition, or by selecting the CANCEL command button 88, which will close the window and abort the definition.

Once templates have been defined for each of the potential conditions to be included within the TS, either by using the method discussed above with reference to FIGS. 5–8 or by alternative means known to those with skill in the art for defining ultrasound measurements and calculations pertinent to the potential conditions to be studied by the system, the TS is stored in the system memory 11 (of FIG. 1) as element 33. As noted, TSs for various ultrasound studies, such as adult cardiac and fetal development, typically may be provided to the user by some convenient means, such as on a CD-ROM. Alternatively, the TS may be created by the user during the system set up.

Figure 9A:
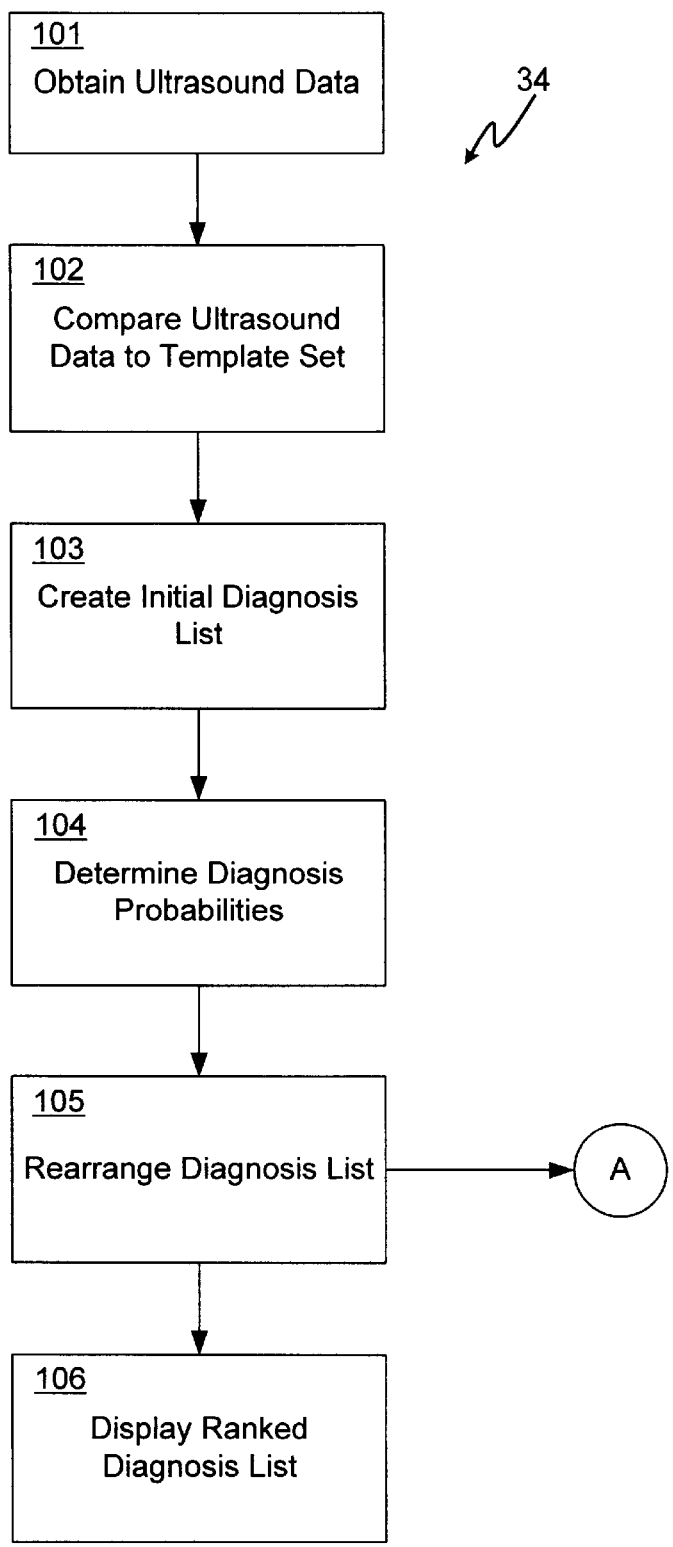
FIGS. 9A, 9B and 9C are flow charts illustrating a method by which the correlation program of FIG. 1 may correlate the ultrasound data obtained from a basic set of ultrasound measurements with the set of templates defined in accordance with FIGS. 5, 6, 7 and 8 to provide the user with a ranked list of potential diagnoses and a ranked list of additional recommended measurements.
Figure 9B:
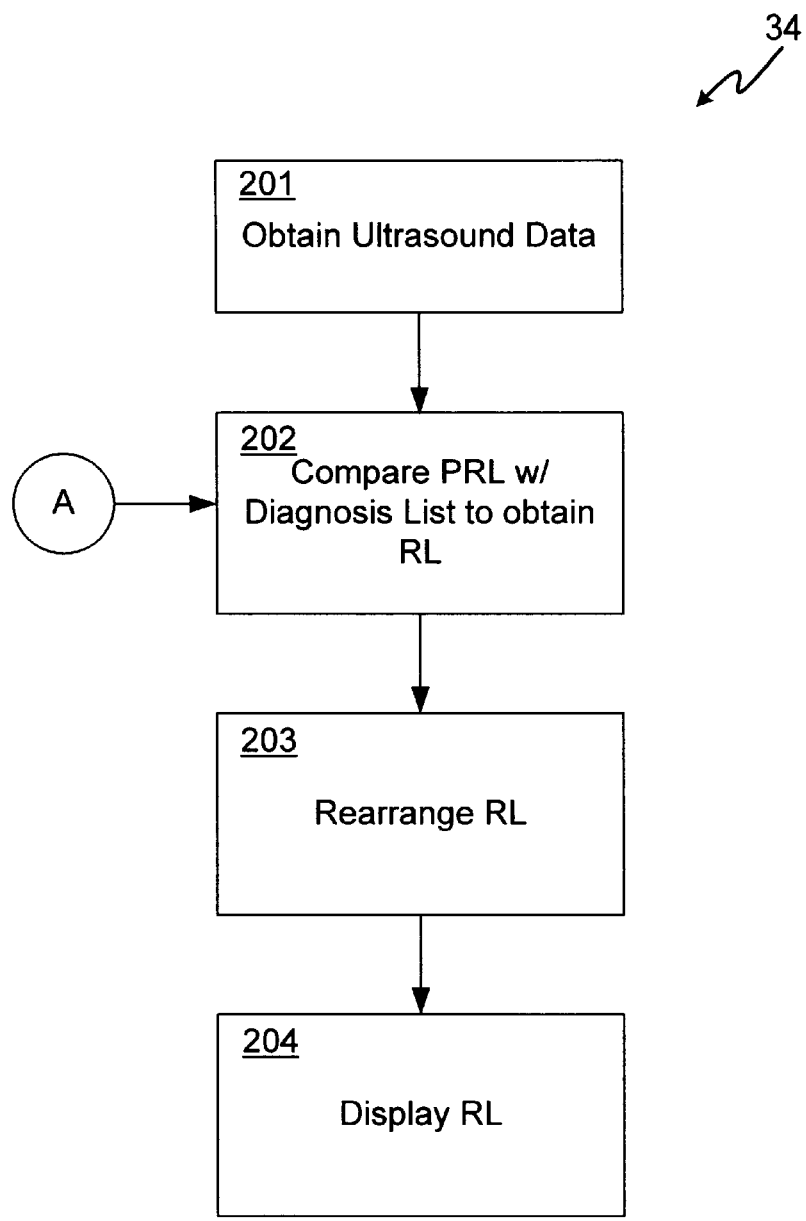
Figure 9C:
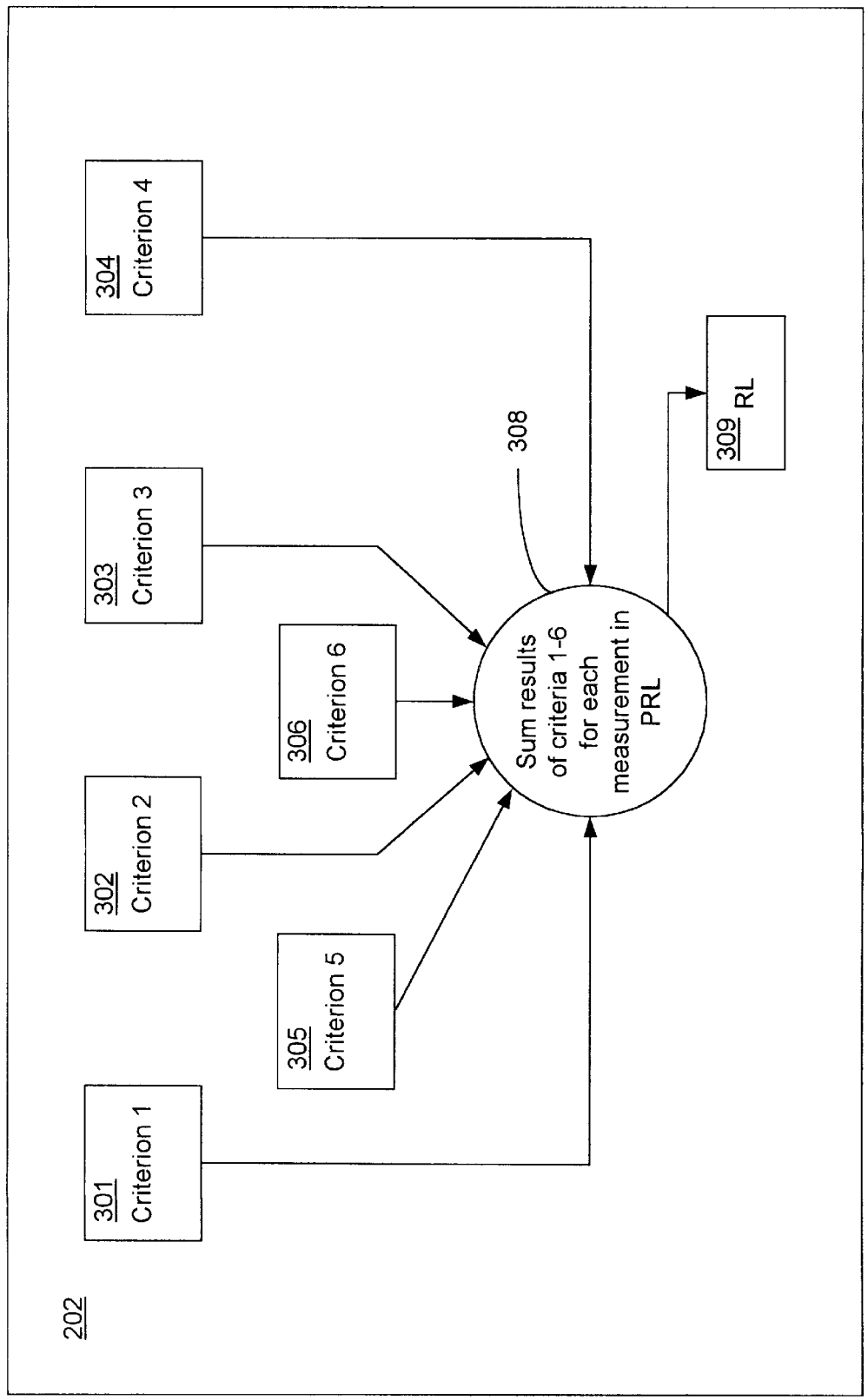

With reference to the flow charts illustrated in FIGS. 9A, 9B and 9C, the following discussion describes an embodiment of the correlation program 34 (of FIG. 1), whereby the ultrasound data obtained from the patient is automatically correlated with the TS to provide the user with a ranked list of potential diagnoses and a ranked list of additional recommended measurements.

The flow charts of FIGS. 9A through 9C show the architecture, functionality, and operation of a possible implementation of the correlation program 34 of FIG. 1. In this regard, each block represents a module, segment, or portion of code, which comprises one or more executable instructions for implementing the specified logical function(s). It should also be noted that in some alternative implementations, the functions noted in the blocks may occur out of the order noted in FIGS. 9A through 9C. For example, two blocks shown in succession in FIGS. 9A through may in fact be executed substantially concurrently or the blocks may sometimes be executed in the reverse order, depending upon the functionality involved.

With reference to FIG. 9A, the correlation program creates a ranked list of potential diagnoses as follows: in step 101, ultrasound data, consisting of various measurements (M) and calculations (C), is obtained from the patient.

In step 102, the program compares the ultrasound data to the TS for a particular ultrasound study, such as adult cardiac. Step 102 may be accomplished by comparing the ultrasound data directly with each diagnosis template in the TS. Alternatively, step 102 may be accomplished by first constructing a focused set from the TS, with the focused set containing only the diagnoses in the TS that are associated with the particular measurements and calculations being performed. The ultrasound data is then compared only with the templates in focused set, and not with the entire TS. In this way, no time is wasted comparing the ultrasound data to templates in the TS for which the particular measurement or calculation is inapplicable, and which therefore cannot yield a positive result. For example, assume that measurement $M_A$ is performed on the patient. Measurement $M_A$ is included only in diagnoses $D_1$, $D_2$ and $D_4$. Therefore, diagnoses $D_1$, $D_2$ and $D_4$ would be the only diagnoses in the focused set. When ultrasound data is obtained for measurement $M_A$, the program would compare that data only to the diagnoses in the focused set and not to the entire TS.

Once step 102 is completed, the program proceeds to step 103, in which the program creates a list of potential diagnoses (i.e., diagnoses for which the ultrasound data indicates a potential abnormal condition). In step 104, the program determines the probability associated with each potential diagnosis on the list, based on the probability associated with each measurement and calculation defined for the template for that diagnosis (such as in field 64 of FIG. 6). In step 105, the program rearranges the diagnosis list in ranked order based on the probability associated with each potential diagnosis, and in step 106, the program displays the ranked list for the user. Steps 104 through 106 may be performed concurrently. The list displayed may be configured to suit the user's preference. Some examples include displaying each potential diagnosis in ranked order, displaying only the five most likely diagnoses in ranked order, and displaying only those diagnoses for which the probability exceeds some threshold.

As additional ultrasound data is obtained from the patient, steps 101 through 106 are repeated, and the program continuously updates the list of potential diagnoses and the rank of the diagnoses on the displayed list.

With reference to FIG. 9B, the correlation program provides the user with a ranked list of additional recommended measurements as follows: in step 201, the measurements in the MS are compared with the measurements included in the TS for the particular ultrasound study being performed (i.e., adult cardiac, fetal development, etc.) to define a potential recommended list ("PRL") of additional measurements. Measurements in the MS that do not occur in the TS are excluded from the PRL.

Once the PRL is determined, in step 202 the correlation program correlates the PRL with the ranked list of potential diagnoses obtained in step 105 of FIG. 9A to narrow the PRL to a recommended list of measurements ("RL"). Then, in step 203 the program automatically re-orders the measurements on the RL so that the most appropriate measurements appear on the list in descending order, and displays the ranked list to the user in step 204. Steps 202, 203 and 204 may be executed concurrently.

FIG. 9C is a flowchart illustrating one embodiment of a method that may be used to implement step 202 of FIG. 9B. With reference to FIG. 9C, a series of ranking criteria 301 through 306 are used for ranking the measurements on the RL. Each potential measurement on the RL is subjected to each of the criteria defined below for steps 301 through 306, which may be executed concurrently or in any order. The results of these steps are summed in step 308 for each measurement. In this example, the results of each of the steps 301 through 306 are each assigned some integer value of points, with the sum of the points for all the steps equaling 100. None of the steps is mutually exclusive with any other step. Therefore, a particular measurement may successfully meet the criteria for each of the steps 301 through 306. If a particular measurement meets the criteria for each step, that measurement is assigned a value of 100 in step 308 (i.e., the sum of the results for each step 301 through 306). If not, the measurement is assigned a value in step 308 that corresponds to the sum of the values for each step for which the measurement satisfies the specified criteria. Once each measurement is assigned a value, the measurements and their corresponding values are placed on the RL in step 309. These values are then used in step 203 of FIG. 9B to rank the measurements on the RL in descending order (i.e., the measurement having the highest aggregate value listed first). Measurements having an aggregate value of zero should not be included on the RL. If desired, a threshold value can be set to eliminate less relevant measurements from the RL as well.

The following is an example of how the flow chart illustrated in FIG. 9C may be used to rank the measurements on the RL. In this example, the first criterion is assigned a value of 29 points. This criterion, which is determined in step 301, is satisfied if a potential measurement is in the template for a diagnosis that has a higher probability of occurring than that of another diagnosis indicated by the same positive measurement from the basic set. As an example, consider Example A as follows:

Example A

| Template for Diagnosis 1 ($D_1$) | Template for Diagnosis 2 ($D_2$) |
|---|---|
| Measurement A ($M_A$) | Measurement C ($M_C$) |
| Measurement B ($M_B$) | Measurement D ($M_D$) |
|  | Measurement A ($M_A$) |

$M_A$ is measured and is considered to be abnormal for both $D_1$ and $D_2$. However, in this example, the likelihood of $D_1$ being present is 50%, while the likelihood of $D_2$ being present is 30%. Therefore, because $D_1$ has a higher probability of occurring than $D_2$, $M_B$ satisfies this criterion and is awarded 29 points.

The second criterion in this example, which is determined in step 302, is assigned a weight of 24 points. This criterion is satisfied if a measurement is indicated in more than one diagnosis on the PRL. As an example, consider Example B as follows:

Example B

| Template for Diagnosis 1 ($D_1$) | Template for Diagnosis 2 ($D_2$) |
|---|---|
| Measurement A ($M_A$) | Measurement C ($M_C$) |
| Measurement B ($M_B$) | Measurement D ($M_D$) |
| Measurement E ($M_E$) | Measurement A ($M_A$) |

Both $M_E$ and $M_D$ have been measured and are considered to be outside of the acceptable boundaries for $D_1$ and $D_2$ respectively. $M_A$ satisfies this criterion because it is indicated in both $D_1$ and $D_2$.

The third criterion in this example, which is determined in step 303, is assigned a weight of 19 points. This criterion is satisfied if an additional measurement for an indicated diagnosis is performed in the current imaging modality (i.e., 2D, M-mode, Doppler). As an example, consider Example C as follows:

Example C

| Diagnosis 1 ($D_1$) | Diagnosis 2 ($D_2$) |
|---|---|
| Measurement A ($M_A$) | Measurement C ($M_C$) |
| Measurement B ($M_B$) | Measurement D ($M_D$) |
| Measurement E ($M_E$) | Measurement A ($M_A$) |

$M_A$ is measured and is considered to be abnormal for both $D_1$ and $D_2$. $M_A$ is measured in 2D. Of the remaining measurements $M_D$ is measured in 2D, $M_B$ is measured in M-mode and $M_C$ and $M_E$ are measured in Doppler. Because $M_D$ is measured in 2D and the user has just completed a measurement in 2D and remains in that imaging modality, $M_D$ satisfies this criterion.

The fourth criterion in this example, which is determined in step 304, is assigned a weight of 14 points. This criterion is satisfied if an additional measurement is the last measurement needed to complete the measurements in the template for an indicated diagnosis. As an example, consider Example D as follows:

Example D

| Diagnosis 1 (D$_1$) | Diagnosis 2 (D$_2$) |
|---|---|
| Measurement A (M$_A$) | Measurement C (M$_C$) |
| Measurement B (M$_B$) | Measurement D (M$_D$) |
|  | Measurement A (M$_A$) |

M$_A$ is measured and is considered to be outside of the acceptable boundaries for both D$_1$ and D$_2$. M$_B$ is the last indicated measurement in the list for D$_1$, whereas D$_2$ requires both M$_C$ and M$_D$. In this case, M$_B$ satisfies this criterion.

The fifth criterion in this example, which is determined in step 305, is assigned a weight of 9 points. This criterion is satisfied if an additional measurement is the last dependent measurement in a calculation that is included in the template of an indicated diagnosis. As an example, consider Example E as follows:

Example E

| Diagnosis 1 (D$_1$) | Diagnosis 2 (D$_2$) |
|---|---|
| Measurement A (M$_A$) | Calculation B (C$_B$) — |
| Measurement F (M$_F$) | (Measurement D (M$_D$) |
| Calculation A (C$_A$) — | Measurement E (M$_E$)) |
| (Measurement B (M$_B$) | Measurement A (M$_A$) |
| Measurement C (M$_C$)) |  |

In this case, M$_A$ is measured and is considered to be outside of the acceptable boundaries for both D$_1$ and D$_2$. Additionally M$_B$ has been measured. C$_A$ has dependent measurements M$_B$ and M$_C$, and C$_B$ has dependent measurements M$_D$ and M$_E$. Since C$_A$ is indicated in D$_1$ and M$_B$ has already been completed, M$_C$ is the only remaining measurement that must be made in order to calculate C$_A$. However, both M$_D$ and M$_E$ must be measured before C$_B$ can be calculated. Therefore, M$_C$ satisfies this criterion.

The sixth and final criterion in this example, which is determined in step 306, is assigned a weight of 5 points. This criterion is satisfied if a measurement is a dependent input of a calculation that is part of the template of an indicated diagnosis. A measurement that entered the list from pass one by being a measurement required to complete a calculation that is indicated in a diagnosis will be ranked higher than those measurements which are not needed in calculations. As an example, consider Example F as follows:

Example F

| Diagnosis 1 (D$_1$) |
|---|
| Measurement A (M$_A$) |
| Measurement F (M$_F$) |
| Calculation A (C$_A$) — |
| (Measurement B (M$_B$) |
| Measurement C (M$_C$)) |

M$_A$ is measured and is considered to be outside of the acceptable boundary for D$_1$. Since M$_B$ and M$_C$ are inputs for C$_A$ both satisfy the criterion and are assigned a value of 5 points each. M$_F$, which is not part of a calculation included in the template for D$_1$ does not satisfy the criterion.

Once points are assigned to each measurement in the PRL based on the six criteria of steps 301 through 306, the points for each measurement and calculation are summed in step 308. The measurements, together with their aggregate sums are listed on the RL in step 309, which completes the illustration of step 202 of FIG. 9B. Once step 202 is completed, step 203 uses the RL of step 202 to rank the measurements on the RL. The ranked RL is displayed to the user in step 204.

The preceding is one illustrative method of determining and assigning relative rankings to the various measurements on the RL. However, other methods may be used to arrive at the rankings and other and different criteria may be used in determining the relative weights to be accorded each measurement on the RL without departing from the invention.

It should be emphasized that the above-described embodiments of the present invention, particularly, any "preferred" embodiments, are merely possible examples of implementations, merely set forth for a clear understanding of the principles of the invention. Many variations and modifications may be made to the above-described embodiment(s) of the invention without departing substantially from the spirit and principles of the invention. All such modifications and variations are intended to be included herein within the scope of the present invention.

What is claimed is:

1. A method for operating an ultrasound measurement system, the method comprising the steps of:

defining a template set of possible diagnoses, said template set comprising at least one template, said at least one template defining the threshold value of at least one ultrasound measurement from a baseline set of ultrasound measurements, said threshold value being indicative of a diagnosis corresponding to that template;

performing a first ultrasound measurement from the baseline set of ultrasound measurements to obtain a first result; and automatically correlating said first result with said template set of possible diagnoses to determine whether any of said possible diagnoses are indicated by said first result.

2. The method of claim 1, further comprising the steps of:

performing a second ultrasound measurement, different from the first ultrasound measurement in either type of measurement and/or physical characteristic being measured, to obtain a second result; and automatically correlating said second result with said template set of possible diagnoses to determine whether any of said possible diagnoses are indicated by said second result.

3. The method of claim 2, further comprising the steps of:

performing a plurality of additional ultrasound measurements to obtain a plurality of results; and automatically correlating said plurality of results with said template set of possible diagnoses to determine the possible diagnoses indicated by said plurality of results.

4. The method of claim 1, further comprising the step of:

compiling a list of possible diagnoses indicated by said correlation.

5. The method of claim 4, further comprising the step of:

determining the relative likelihood of each potential diagnosis on said list.

6. The method of claim 5, further comprising the step of:

organizing the potential diagnoses on said list according to the relative likelihood of each potential diagnosis.

7. The method of claim 4, further comprising the step of:

automatically correlating said list of possible diagnoses with said template set to recommend additional ultrasound measurements relevant to the possible diagnoses on said list.

8. An ultrasound measurement system comprising:

means for obtaining ultrasound data corresponding to at least one ultrasound measurement from a baseline set of ultrasound measurements;

means for accessing a template set of possible diagnoses, said template set comprising at least one template, said at least one template defining the threshold value of at least one ultrasound measurement from the baseline set of ultrasound measurements, said threshold value being indicative of the diagnosis corresponding to that template; and means for automatically correlating said ultrasound data with said template set of possible diagnoses to determine whether any of said possible diagnoses are indicated by said ultrasound data.

9. The system of claim 8, further comprising:

means for compiling a list of possible diagnosis indicated by said correlating means.

10. The system of claim 9, further comprising:

means for making said list available to the system user.

11. The system of claim 9, further comprising:

means for determining the relative likelihood of each possible diagnosis on said list; and means for organizing the potential diagnoses on said list according to the relative likelihood of each potential diagnosis.

12. The system of claim 11, further comprising:

means for automatically correlating said organized list of possible diagnoses with said template set to compile a list of recommend additional ultrasound measurements relevant to the possible diagnoses on said organized list.

13. The system of claim 12, further comprising:

means for ranking the measurements on said list of recommended additional measurements according to their respective importance to confirming the possible diagnoses on said organized list.

14. A computer readable medium having a program for operating an ultrasound measurement system, the program comprising:

means for obtaining ultrasound data corresponding to at least one ultrasound measurement from a baseline set of ultrasound measurements;

means for accessing a template set of possible diagnoses, said template set comprising at least one template, said at least one template defining the threshold value of at least one ultrasound measurement from the baseline set of ultrasound measurements, said threshold value being indicative of the diagnosis corresponding to that template; and means for automatically correlating said ultrasound data with said template set of possible diagnoses to determine whether any of said possible diagnoses are indicated by said ultrasound data.

15. The program of claim 14, further comprising:

means for compiling a list of possible diagnosis indicated by said correlating means.

16. The program of claim 15, further comprising:

means for determining the relative likelihood of each possible diagnosis on said list; and means for organizing the potential diagnoses on said list according to the relative likelihood of each potential diagnosis.

17. The program of claim 16, further comprising:

display means for providing said organized list to a system user.

18. The program of claim 16, further comprising:

means for automatically correlating said organized list of possible diagnoses with said template set to compile a list of recommend additional ultrasound measurements relevant to the possible diagnoses on said organized list.

19. The program of claim 18, further comprising:

means for ranking the measurements on said list of recommended additional measurements according to their respective importance to confirming the diagnoses on said organized list.

20. The program of claim 19, further comprising:

display means for providing said organized list of recommended additional measurements to a system user.

21. An diagnostic system comprising:

an ultrasound imaging system that scans a patient and outputs measurements of physical characteristics of the patient;

a database containing a set of templates of possible diagnoses, each template defining a threshold value of at least one baseline measurement, said threshold value being indicative of a diagnosis corresponding to that template; and a control program that receives a measurement from the ultrasound imaging system, retrieves templates from the database which have a threshold value listed for the received measurement and cross references the retrieved templates with at least one measurement from the ultrasound imaging system to offer a possible diagnosis.

22. A diagnostic system, as set forth in claim 21, wherein said templates define threshold values for calculations based on the measurements.

23. A diagnostic system, as set forth in claim 21, wherein said control program operates in real time with the scanning of the patient.

24. A diagnostic system, as set forth in claim 23, wherein said control program analyzes the retrieved templates and identifies additional measurements that would refine the possible diagnosis and suggest to a user that the additional measurements be performed.

* * * * *